US00PP27409P3

(12) United States Plant Patent
Valin

(10) Patent No.: US PP27,409 P3
(45) Date of Patent: Nov. 22, 2016

(54) ***BEGONIA* PLANT NAMED 'TMBG0802'**

(50) Latin Name: *Begonia×tuberhybrida*
Varietal Denomination: TMBG0802

(71) Applicant: Charles Valin, Ipswich (GB)

(72) Inventor: Charles Valin, Ipswich (GB)

(73) Assignee: Branded Garden Products Ltd., Ipswich, Sulfolk (GB)

( * ) Notice: Subject to any disclaimer, the term of this patent is extended or adjusted under 35 U.S.C. 154(b) by 6 days.

(21) Appl. No.: 14/545,195

(22) Filed: Apr. 4, 2015

(65) Prior Publication Data

US 2016/0295781 P1 Oct. 6, 2016

(51) Int. Cl.
*A01H 5/02* (2006.01)

(52) U.S. Cl.
USPC ..... Plt./343

(58) Field of Classification Search
USPC ..... Plt./343
CPC ..... A01H 5/0238
See application file for complete search history.

*Primary Examiner* — Kent L Bell
(74) *Attorney, Agent, or Firm* — C. A. Whealy

(57) ABSTRACT

A new and distinct cultivar of *Begonia* plant named 'TMBG0802', characterized by its upright to spreading and mounded plant habit; moderately freely basal branching habit; freely and continuously flowering habit; strongly fragrant flowers; and double and single-type flowers that are yellow to apricot in color with a light salmon orange-colored reverse.

2 Drawing Sheets

Botanical designation: *Begonia×tuberhybrida.*
Cultivar denomination: 'TMBG0802'.

CROSS-REFERENCED TO CLOSELY-RELATED APPLICATIONS

Title: *Begonia* Plant Named 'TMBG0822'.
Applicant: Charles Valin
Filed: Concurrently with this application, U.S. Plant patent application Ser. No. 14/545,183.

BACKGROUND OF THE INVENTION

The present invention relates to a new and distinct cultivar of *Begonia* plant, botanically known as *Begonia×tuberhybrida*, and hereinafter referred to by the name 'TMBG0802'.

The new *Begonia* plant is a product of a planned breeding program conducted by the Inventor in Harkstead, Ipswich, United Kingdom. The objective of the breeding program was to develop new trailing *Begonia* plants with fragrant flowers.

The new *Begonia* plant originated from a self-pollination made by the Inventor in August, 2007 of a proprietary selection of *Begonia×tuberhybrida* identified as code number BG #001, not patented. The new *Begonia* plant was discovered and selected by the Inventor as a single flowering plant from within the progeny of the stated self-pollination in a controlled greenhouse environment in Harkstead, Ipswich, United Kingdom in July, 2008.

Asexual reproduction of the new *Begonia* plant by shoot tip cuttings in a controlled greenhouse environment in Harkstead, Ipswich, United Kingdom since August, 2008 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'TMBG0802'. These characteristics in combination distinguish 'TMBG0802' as a new and distinct *Begonia* plant:

1. Upright to spreading and mounded plant habit.
2. Moderately freely basal branching habit.
3. Freely and continuously flowering habit.
4. Strongly fragrant flowers.
5. Double and single-type flowers that are yellow to apricot in color with a light salmon orange-colored reverse.

Plants of the new *Begonia* can be compared to plants of the parent selection. Plants of the new *Begonia* differ from plants of the parent selection in the following characteristics:

1. Leaves of plants of the new *Begonia* are darker green in color than leaves of plants of the parent selection.
2. Plants of the new *Begonia* are more freely flowering than plants of the parent selection.
3. Flowers of plants of the new *Begonia* are more fragrant than flowers of plants of the parent selection.
4. Plants of the new *Begonia* and the parent selection differ in flower color as flowers of plants of the parent selection do not have a light salmon-colored reverse.

Plants of the new *Begonia* can be compared to plants of *Begonia×tuberhybrida* 'TMBG0822', disclosed in U.S. Plant patent application Ser. No. 14/545,183. Plants of the new *Begonia* differ primarily from plants of 'TMBG0822' in flower color as plants of 'TMBG0822' have lemon yellow-colored flowers with a light orange-colored reverse. In addition, plants of the new *Begonia* produce male and female flowers whereas plants of 'TMBG0822' only produce male flowers.

Plants of the new *Begonia* can also be compared to plants of the *Begonia pendula* 'Victoria Falls', disclosed in U.S.

Plant Pat. No. 20,653. In side-by-side comparisons conducted in Harkstead, Ipswich, United Kingdom, plants of the new *Begonia* differed from plants of 'Victoria Falls' in the following characteristics:

1. Plants of the new *Begonia* had larger flowers than plants of 'Victoria Falls'.
2. Flowers of plants of the new *Begonia* were more fragrant than flowers of plants of 'Victoria Falls'.
3. Plants of the new *Begonia* and 'Victoria Falls' differed in flower color as plants of 'Victoria Falls' had bright orange-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'TMBG0802' grown in a container.

The photograph on the second sheet are close up views of upper and lower surfaces of typical double flowers, single flowers and leaves of 'TMBG0802'.

DETAILED BOTANICAL DESCRIPTIONS

Plants used for the aforementioned photographs and following observations and measurements were grown in 12-cm containers during the winter in a glass-covered greenhouse in Maasdijk, The Netherlands. During the production of the plants, day temperatures ranged from 19° C. to 21° C., night temperatures ranged from 18° C. to 20° C. and light levels averaged 6,000 lux. Plants were eight weeks old when the photographs and the description were taken. In the following description, color references are made to The Royal Horticultural Society Colour Chart, 2007 Edition, except where general terms of ordinary dictionary significance are used.

Botanical classification: *Begonia×tuberhybrida* 'TMBG0802'.

Parentage:

*Female, or seed, parent*.—Proprietary selection of *Begonia×tuberhybrida* identified as code number BG #001, not patented.

*Male, or pollen, parent*.—Proprietary selection of *Begonia×tuberhybrida* identified as code number BG #001, not patented.

Propagation:

*Type*.—By shoot tip cuttings.

*Time to initiate roots, summer*.—About 20 days at temperatures of about 20° C. to 23° C.

*Time to initiate roots, winter*.—About 22 days at temperatures of about 20° C. to 23° C.

*Time to produce a rooted young plant, summer*.—About 35 days at temperatures of about 20° C. to 23° C.

*Time to produce a rooted young plant, winter*.—About 35 to 38 days at temperatures of about 20° C. to 23° C.

*Root description*.—Thin, fibrous; light brown in color; plants of the new *Begonia* have not been observed to form tubers.

*Rooting habit*.—Moderately freely branching; medium density.

Plant description:

*Plant form and growth habit*.—Upright to spreading and mounded plant habit; flattened globular in shape; moderately freely basal branching with about four primary branches per plant; primary branches with secondary branches at potentially every node; moderately vigorous growth habit.

*Plant height*.—About 14.5 cm.

*Plant width*.—About 22.4 cm.

*Lateral branch description*.—Length: About 4.6 cm. Diameter: About 8 mm. Internode length: About 8 mm. Aspect: About 40° from vertical. Texture: Sparsely pubescent. Color, developed: Close to 146A. Color, developed: Darker than between 146A and 148A.

*Leaf description*.—Arrangement: Alternate, simple. Length: About 10.6 cm. Width: About 5.2 cm. Shape: Ovate to narrowly ovate. Apex: Acute. Base: Unequal hastate. Margin: Bi-serrate. Texture, upper and lower surfaces: Sparsely pubescent; velvety. Venation pattern: Palmate; reticulate. Color: Developing leaves, upper surface: Close to between 147A and 203A. Developing leaves, lower surface: Close to 187C. Fully expanded leaves, upper surface: Darker than N189A; venation, close to 146A. Fully expanded leaves, lower surface: Close to 183B; venation, close to 146A. Petioles: Length: About 4.4 cm. Diameter: About 4 mm. Texture, upper and lower surfaces: Moderately pubescent. Color, upper surface: Close to 174A; distally, close to 183A. Color, lower surface: Close to 165A; distally, close to 183A.

Flower description:

*Flowering habit*.—Double (male) and single-type (female) rotate flowers arranged in axillary cymes; freely flowering habit with about two flowers (typically one male and one female flower) per cyme and about 32 flowers developing per plant; flowers face mostly outwardly to slightly nodding.

*Fragrance*.—Strongly fragrant; fragrance pleasant, sweetly acidic; similar to rose and citrus.

*Natural flowering season*.—Plants begin flowering about four to six weeks after planting; long flowering period, in the garden plants flower freely and continuously from spring until autumn in The Netherlands and plants can be flowered year-round in greenhouses.

*Flower longevity*.—Individual flowers last about ten days on the plant; flowers not persistent.

*Inflorescence height (including peduncle)*.—About 13.1 cm.

*Inflorescence diameter*.—About 9.3 cm.

*Flower buds*.—Length: About 2.8 cm. Diameter: About 1.1 cm to 2.3 cm. Shape: Obovate to nearly circular, flattened. Color: Close to 41C to 41D; towards the margins, close to 42B.

*Flowers*.—Female flowers, diameter: About 5.7 cm. Female flowers, depth (height): About 2 cm. Male flowers, diameter: About 8.5 cm. Male flowers, depth (height): About 4 cm.

*Tepals*.—Quantity per flower: Female flowers, usually about five per flower in a single whorl; male flowers, usually about two per flower. Length, female flowers: About 3.2 cm. Width, female flowers: About 2.5 cm. Length, male flowers: About 4.5 cm. Width, male flowers: About 5 cm. Shape, female flowers: Obovate. Shape, male flowers: Nearly orbicular. Apex, female flowers: Obtuse to broadly acute. Apex, male flowers: Obtuse, rounded. Margin, female flowers: Entire. Margin, male flowers: Entire to irregularly finely crenate. Texture, female and male flowers, upper surface: Smooth, glabrous; velvety. Texture, female and male flowers, lower surface: Smooth, glabrous; slightly velvety. Color, female and male flowers: When opening, upper surface: Close to 11B to 11C; towards the margins, tinged with close to 31A and 31B; toward the base, close to 2D. When opening, lower surface: Close to N34B to N34D. Fully opened, upper surface: Close to 11C to 11D; towards the margins, tinged with close to 29C; color does not fade with development. Fully opened, lower surface: Close to N34B; color does not fade with development.

*Tepaloids*.—Quantity per flower: Present only on male flowers, usually about 40 per flower. Length: About 1.5 cm to 4.3 cm. Width: About 0.9 cm to 3.3 cm. Shape: Obcordate. Apex: Obtuse. Margin: Entire. Texture, upper surface: Smooth, glabrous; velvety. Texture, lower surface: Smooth, glabrous; slightly velvety. Color: When opening, upper surface: Close to 155D; towards the apex, tinged with close to 11D. When opening, lower surface: Close to 27C to 27D; towards the base, close to 155D. Fully opened, upper surface: Close to 11D; towards the margins, tinged with close to 27C; towards the apex, tinged with close to 29B; color does not fade with development. Fully opened, lower surface: Close to 29C; color does not fade with development.

*Peduncles*.—Length: About 6.2 cm. Diameter: About 5 mm. Angle: Varying between 30° to 60° from vertical. Strength: Moderately strong. Texture: Sparsely pubescent. Color: Close to 152A; proximally, tinged with close to N199C.

*Pedicels*.—Length: About 3.8 cm. Diameter: About 3 mm. Aspect: About 25° from peduncle axis. Strength: Moderately strong. Texture, female flowers: Densely pubescent. Texture, male flowers: Sparsely pubescent. Color, upper surface (exposed to the light): Close to 171A. Color, lower surface: Close to N170B.

*Reproductive organs*.—Female flowers: Number of pistils: About six per flower arranged in pairs. Pistil length: About 8 mm. Style length: About 7 mm. Style color: Close to 14B. Stigma color: Close to 17B. Ovary color: Close to 145A; wings, close to 42B to 42C. Male flowers: All stamens on male flowers transformed into tepaloids. Seeds and fruits: Seed and fruit production has not been observed on plants of the new *Begonia*.

Disease & pest resistance: Resistance to pathogens and pests common to *Begonia* plants has not been observed on plants of the new *Begonia*.

Temperature tolerance: Plants of the new *Begonia* have been observed to tolerate temperatures from about 10° C. to about 35° C.

It is claimed:

1. A new and distinct *Begonia* plant named 'TMBG0802' as illustrated and described.

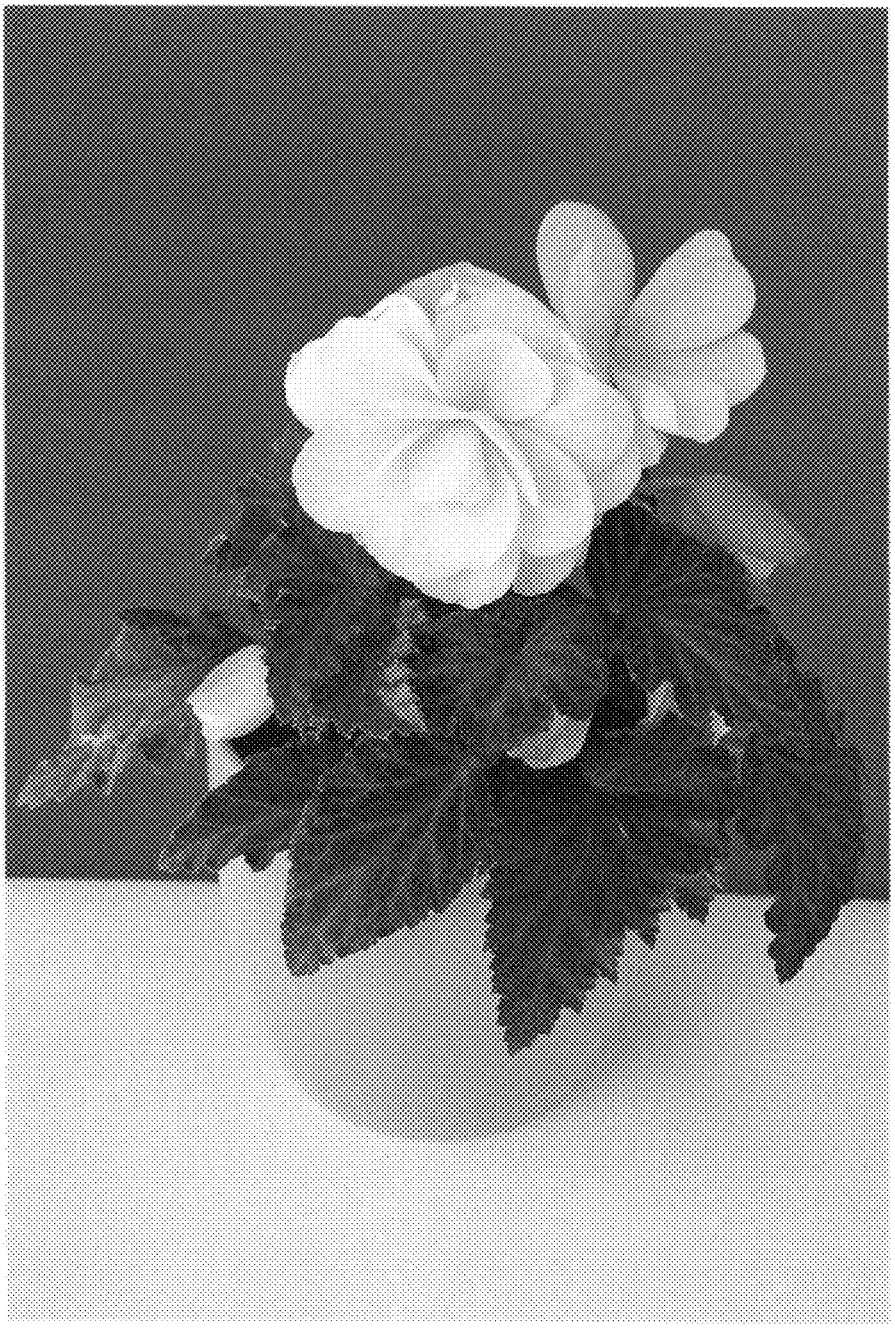

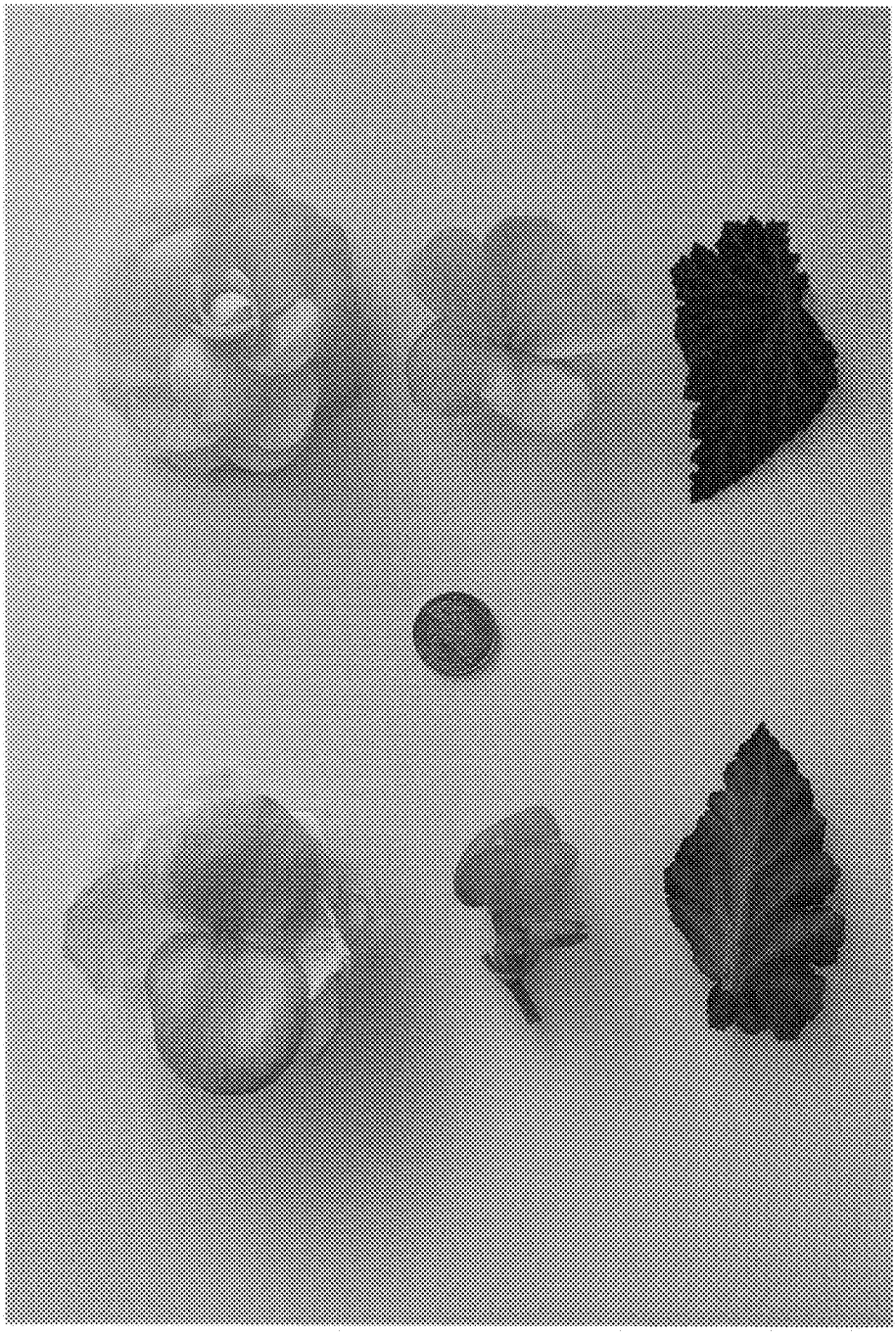

* * * * *